US008883433B2

(12) United States Patent
Mirshahi et al.

(10) Patent No.: US 8,883,433 B2
(45) Date of Patent: Nov. 11, 2014

(54) METHOD FOR IN VITRO ASSAY OF SOLUBLE FIBRIN BY GENERATING SPECIFIC DEGRADATION PRODUCTS

(75) Inventors: Bibi Shah Soltan Mirshahi, Villejuif (FR); Jeannette Soria, Taverny (FR)

(73) Assignees: Societe Diagnostica-Stago (FR); Assistance Publique-Hopitaux de Paris (FR)

( * ) Notice: Subject to any disclaimer, the term of this patent is extended or adjusted under 35 U.S.C. 154(b) by 1096 days.

(21) Appl. No.: 10/373,614

(22) Filed: Feb. 25, 2003

(65) Prior Publication Data
US 2003/0175839 A1   Sep. 18, 2003

Related U.S. Application Data

(63) Continuation of application No. PCT/FR01/02628, filed on Aug. 17, 2001.

(30) Foreign Application Priority Data

Aug. 28, 2000   (FR) ...................................... 00 10999

(51) Int. Cl.
G01N 33/86 (2006.01)
G01N 33/53 (2006.01)

(52) U.S. Cl.
CPC ...................................... *G01N 33/86* (2013.01)
USPC .............................. 435/7.92; 435/7.1; 435/13

(58) Field of Classification Search
None
See application file for complete search history.

(56) References Cited

U.S. PATENT DOCUMENTS

| 4,957,903 | A | * | 9/1990 | Ranby | 514/18 |
| 5,041,376 | A | * | 8/1991 | Gething et al. | 435/6 |
| 5,114,845 | A | * | 5/1992 | Ranby | 435/13 |
| 5,175,087 | A | * | 12/1992 | Ranby et al. | 435/13 |
| 5,206,140 | A | * | 4/1993 | Marder et al. | 435/7.1 |
| 5,453,359 | A | | 9/1995 | Gargan et al. | |
| 5,821,068 | A | * | 10/1998 | Soe et al. | 435/7.21 |
| 6,048,684 | A | | 4/2000 | Becker et al. | |
| 7,968,302 | B2 | | 6/2011 | Mirshahi et al. | |

FOREIGN PATENT DOCUMENTS

| EP | 0 576 038 A2 | 12/1993 |
| EP | 0 347 933 A3 | 12/1999 |
| WO | 02/18628 A1 | 3/2002 |

OTHER PUBLICATIONS

Barro et al, "Plasma D-dimers: comparison of ELISA with a new, rapid, quantitative latex assay," (Clin. Lab. Haem.) 1999, vol. 21, pp. 363-364.*
Winman et al., Determination of Soluble Fibrin in Plasma by a Rapid and Quantitative Spectrophotometric Assay, Thromb Haemostasis, 1986, vol. 55, No. 2, pp. 189-193.
Collen et al., Recombinant Staphylokinase Variants with Altered Ammumoreactivity, Circulation, 1996, vol. 94, No. 2, pp. 197-206.
Godal et al., Gelation of Soluble Fibrin in Plasma by Ethanol, Scand. J. Haemat, 1966, vol. 3, pp. 342-350.
Breen et al., Ethanol Gelation: A Rapid Screening Test for Intravascular Coagulation, Annals of Internal Medicine, 1968. vol. 69, No. 6, pp. 1997-1206.
Seaman et al., The Recognition of Intravascular Clotting, Arch Internal medicine, 1970, vol. 125, pp. 1016-1021.
Lipinski et al.. Detection of soluble fibrin monomer complexes in blood by means of protamine sulphate test, Dep. of Physiological Chem. Medical School, Bialystok Poland, date unknown, pp. 44-49.
Latallo et al., Effects of protamine sulphate on the solubility of fibrinogen, its derivates and other plasma proteins, Dept. of Radiobiology and Health Protections, Institute of Nuclear Research, Warsaw Poland, date unknown, pp. 151-162.
Musemeci, V., Ethanol gelation test and protamine sulphate test in diagnosis of intravascular coagulation, Laboratory of blood coagulation, Department of Internal Medicine, Universita Cattolica, Roma Italy, date unknown, pp. 197-202.
Gurewich et al., The resistance of fibrinogen and soluble fibrin monomer in blood to degradation by a potent plasminogen activator derived from cadaver limbs, Blood, 1975, vol. 46, No. 4, pp. 555-565.
Niewiarowski et al., Laboratory identification of intravascular coagulation, J. Lab. Clin. Med. 1971 pp. 665-676.
Kidder et al., The plasma protamine paracoagulation test: clinical and laboratory evaluation, A.J.C.P. 1972, vol. 58, pp. 675-686.
Gurewich et al., A comparative study of precipitation and paracoagulation by protamine sulfate and ethanol gelation tests, Thrombosis Research, 1973, vol. 2, pp. 539-556.
Gerrits et al., Causes of a negative ethanol gelation test in diffuse intravascular coagulation, Thrombos, Diathes, Haemorr, 1974, vol. 31, pp. 299-308.
Largo et al., Detection of soluble intermediates of the fibrinogen-fibrin conversion using erythrocytes coated with fibrin monomers, Blood 1976 vol. 47, No. 6, pp. 991-1002.
Soria et al., Recherche des complexes solubles de fibrine par un tests d'hemagglutination, La Nouvelle Press Medicale, 1977, vol. 6, No. 43, pp. 4045-4048.
Dempfle et al., Binding of a new monoclonal antibody against n-terminal heptapeptide of fibrin a-chain to fibrin polymerization site A: effects of fibrogen and fibrinogen derivatives, and pretreatment of samples with NaSCN, Blood Coagulation and Fibrinolysis, 1993, vol. 4, pp. 79-86.
Soe et al., A monoclonal antibody that recognizes a neo-antigen exposed in the E domain of fibrin monomer complexed with fibrinogen or its derivates: its application to the measurement of soluble fibrin in plasma, Blood 1996, vol. 88, No. 6, pp. 2109-2117.

(Continued)

*Primary Examiner* — Lisa J Hobbs
(74) *Attorney, Agent, or Firm* — Lerner, David, Littenberg, Krumholz & Mentlik, LLP

(57) ABSTRACT

The invention concerns a method for assaying soluble fibrin in a sample, in which said sample is brought into the presence of a plasminogen activator with a high specificity for soluble fibrin (PA-Fb sp) and the soluble fibrin count in the sample is measured by measuring the difference between the count of fibrin degradation products obtained after degrading soluble fibrin with PA-Fb sp and the base count of fibrin degradation products determined before bringing the sample into the presence of PA-Fb sp.

11 Claims, No Drawings

(56) References Cited

OTHER PUBLICATIONS

Cannon et al., TNK-Tissue plasminogen activator compared with front-loaded alteplase in acute myoardial infarction. Circulation 1998, vol. 98, pp. 2805-2814.

Bringmenn et al., Structural features mediating fibrin selectivity of vampire bat plasminogen activators, J. Biological Chemistry, 1995, vol. 270, No. 43, pp. 25596-25603.

Collen, Desire, Staphylokinase: a potent, uniquely fibrin-selective thrombolytic agent, Nature Medicine 1998, vol. 4, No. 3, pp. 279-284.

Sakharov et al., Fibrin-specificty of a plasminogen activator affects the efficiency of fibrinolysis and responsiveness to ultrasound: comparison of nine plasminogen activators in vitro, Thromb Haemost, 1999, vol. 81, pp. 605-612.

Brenner et al., 'Quantitation of Venous Clot Lysis With the D-Dimer Immunoassay During Fibrinolytic Therapy Requires Correction for Soluble Fibrin Degradation', Circulation 1990;81:1818-1825.

Lipinski et al., Detection of soluble fibrin monomer complexes in blood by means of protamine sulphate test, Thromb. Diath. Haemorrh., 20; 44-49 (1968).

Latallo et al., Effects of protamine sulphate on the solubility of fibrinogen, its derivates and other plasma proteins, Scand. J. Haematol., suppl., 13; 51-162 (1971).

Musemeci, V., Ethanol gelation test and protamine sulphate test in diagnosis of intravascular coagulation, Laboratory of blood coagulation, Scand. J. Haematol., suppl. 12; 197-202 (1971).

Scott K. Brimble et al., "Evaluation of the Combination of a Bedside D-Dimer Assay and Enzyme-Linked Immunosorbent Soluble Fibrin Assay inPatients with Suspected Venous Thromboembolism", Thrombosis Research, Nov. 1, 1997, pp. 291-297, vol. 88, No. 3, Elsevier Science Ltd., USA.

Satoshi Ota et al., "Diagnosis of Deep Vein Thrombosis by Plasma-Soluble Fibrin or D-Dimer", American Journal of Hematology, Aug. 2005, pp. 274-280, vol. 79, No. 4, Wiley-Liss, Inc.

Y.S. Arkel et al., "The use of coagulation activation markers (soluble fibrin polymer, TpPTM, prothrombin fragment 1.2, thrombin-antithrombin, and D-dimer) in the assessment of hypercoagulability in patients with inherited and acquired prothromboticdisorders", Blood Coagulation and Fibrinolysis, Apr. 2002, pp. 199-205, vol. 13, No. 3, Lippincott Williams & Wilkins. (abstract only).

French Preliminary Search Report and Written Opinion, mailed Dec. 12, 2006 in corresponding French Patent Application No. FR 0604072.

International Search Report dated Sep. 28, 2007, in PCT application PCT/FR07/00764.

Bounameaux et al.. J. Mal Vasco 1991; 16:133-6.
Brummel et al., J Biol Chern, 1999; 274: 22862-22870.
Dempfle et al., Fibrinolysis. 1993; 4:79-86.
Dempfle et al., Thromb Haemost., 1995; 74:673-9.
Ginsberg et al., Thromb Haemost. 1995; 74:833-6.
Ginsberg et al., Thromb Haemost. 1996; 75:551-4.
Kevorkian et al., Lancet. 1998; 351: 571-2.
LaCapra et al., Blood Coagul Fibrinolysis. 2000; 11 :371-7.
Lee et al. Thrombosis, and Vascular Biology. 1997, 17: 628-633.
Nieuwenhuizen et al., Blood Coagul Fibrinolysis. 1993; 4:93-6.
Nieuwenhuizen et al., Thromb Haemost. 1992; 68:273-7.
Nossel et al., J Clin Invest. 1974; 54:43-53.
Okajima et al., Am J Hematol. 1996; 51:186-91.
Reber et al., Thromb Haemost. 1999; 81:221-3.
Scarano et al., Fibrinolysis. 1999; 10:245-50.
Shifman et al., J Biol Chem. 1982; 257 :3243-8.
van Beek et al., Br J Haematol. 1996; 92:725-32.
Hart et al., "The detection of D-dimer in plasma by enzyme immunoassay: improved discrimination is obtained with a more specific signal antibody", Blood Coagulation and Fibrinolysis, vol. 5, 1994, pp. 227-232.

* cited by examiner

METHOD FOR IN VITRO ASSAY OF SOLUBLE FIBRIN BY GENERATING SPECIFIC DEGRADATION PRODUCTS

CROSS REFERENCE TO RELATED APPLICATIONS

The present application is a continuation of International Application No. PCT/FR01/02628, filed Aug. 17, 2001, which was published in French, which claims priority from French Application No. 00/10999, filed Aug. 28, 2000, all of which are incorporated herein by reference.

The present invention relates to a method for assaying soluble fibrin by generating specific degradation products in a blood sample.

When coagulation is activated, thrombin is generated that causes the formation of fibrin deposits and the formation of soluble fibrin.

Thrombin detaches fibrinopeptide A from the fibrinogen molecule, causing the generation of fibrin monomers on which the "A" polymerisation sites, which were masked in the fibrinogen, are unmasked, causing an interaction between the "A" sites of the fibrin monomer with accessible "a" sites on both fibrinogen and on fibrin. Next, fibrinopeptide B is liberated, causing "B" polymerisation sites to be unmasked, causing an interaction between the "B" sites of a molecule of fibrin monomer with accessible "b" sites on both fibrinogen and fibrin monomers.

When the quantity of thrombin is very high (in vitro tests), all of the fibrinogen is transformed into fibrin monomers, which then polymerise by interaction of sites "A" and "a", and "B" with "b", to produce a clot of fibrin. In vivo, however, much less thrombin is generated. The generation of fibrin monomers is much less explosive and thus, a portion of the fibrin monomers will polymerise to produce fibrin (thrombus) and a further portion will react with fibrinogen where sites a and b are accessible or with fibrinogen degradation products to produce a soluble fibrin in which fibrin monomers are associated with fibrinogen.

Soluble fibrin is determined in order to study whether coagulation activation exists in a patient, the presence of soluble fibrin in the blood, in particular in plasma, providing evidence for such activation.

This determination is a necessary complement to assaying D-dimers formed by fibrinolysis of the fibrin constituting the thrombus, which is also a marker of the coagulation activation process. The D-dimer count in plasma is increased when the clot degrades in vivo. For this reason, if thrombus is present and is in the process of degrading, the D-dimer count will be increased, regardless of whether coagulation persists or is stopped; in contrast, the soluble fibrin count does not increase any more if coagulation is stopped and in contrast, will increase if coagulation persists.

Specific measurement of the soluble fibrin content in plasma with respect to the D-dimer count thus allows:

1. determination of whether a coagulation process is present in a patient at the moment the sample is taken;
2. evaluation of the coagulo-lytic balance. The base D-dimer count is a reflection of thrombus degradation in vivo; the D-dimer count obtained after adding the thrombolytic agent to the plasma represents the sum of the base D-dimers and that originating from degradation of the fibrin in circulation (or soluble fibrin).

The earliest methods for assaying fibrin that can be cited include the ethanol test (1, 2, 9) or the protamine sulphate test (3, 4, 5, 7). However, those tests are not very specific (9, 10) and not very sensitive (10). Further, large fibrinogen counts (>5 g/l) perturb the results obtained with ethanol tests and with protamine sulphate tests. Finally, the protamine sulphate test results can be difficult to interpret (6, 8).

A further method for detecting soluble fibrin is based on a technique for haemagglutination of red corpuscles sensitised with fibrin monomers using the method described by Largo (11, 12). That type of test is, for example, sold by Diagnostica Stago as the FS Test.

That technique, while it is very simple, can sometimes lack sensitivity and lends itself in particular to diagnosis of disseminated intravascular coagulation. However, it cannot detect smaller amounts of soluble fibrin (local thromboses, exploring the effectiveness of an anti-coagulating drug).

Currently, other techniques for assaying soluble fibrin are based on the use of monoclonal antibodies detecting unmasked epitopes in fibrin and masked in fibrinogen or the products of fibrin or fibrinogen degradation (13-14). However, direct assay using monoclonal antibodies results in soluble fibrin counts that vary depending on the commercial antibody used.

The authors of the present invention propose an approach that differs from those of the prior art, that is particularly simple and rapid, to evaluate the coagulo-lytic balance in a patient. This is more sensitive than the haemagglutination method described above. It has the advantage, compared with tests using monoclonal antibodies, of employing the same manner to detect circulating fibrin (soluble) and that already degraded in vivo, thus providing a very precise evaluation of the coagulo-lytic balance.

In the method of the present invention, the soluble fibrin present in a sample is measured after generating soluble fibrin degradation products, during incubation of the sample with a plasminogen activator with a high specificity and/or high affinity for fibrin (PA-Fb sp). The difference between the count of degradation products obtained after degradation of soluble fibrin with PA-Fb sp and that of the degradation products of the base fibrin, measured before bringing the sample into contact with the PA-Fb sp, allows the plasmatic soluble fibrin count in the sample to be measured.

Thus, the invention provides a method for assaying soluble fibrin in a biological sample, in which said sample is brought into the presence of a plasminogen activator with a high specificity and/or high affinity for fibrin (PA-Fb sp) and the soluble fibrin count in the sample is measured by measuring the difference between the count of degradation products obtained after degrading soluble fibrin with PA-Fb sp and the base count of fibrin degradation products determined for said sample before bringing it into the presence of PA-Fb sp.

The method for assaying soluble fibrin of the invention in a biological sample comprises the steps of:
- assaying the fibrin degradation products contained in a plasma sample;
- bringing the blood plasma sample into contact with a Pa-Fb under conditions that can degrade the soluble fibrin contained in the sample into its degradation products;
- assaying the fibrin degradation products in the sample incubated with Pa-Fb sp;
- determining the soluble fibrin corresponding to the difference between the count of fibrin degradation products evaluated after incubation with PA-Fb sp and the count of fibrin degradation products, evaluated in the untreated sample.

The reagent used to assay the degradation products is selected to measure a given group of degradation products. As an example, antibodies with a set specificity for a particular type of degradation products is used.

The biological sample is preferably a biological liquid, for example a blood or plasma sample, or from drainage.

The invention also concerns the use of a plasminogen activator with a high specificity and/or high affinity for fibrin (i.e., which only activates the plasminogen in the fibrin) in a method for assaying soluble fibrin by generating specific degradation products. It also concerns a kit for carrying out the method described above.

A number of plasminogen activators are known. Certain, however, degrade both fibrinogen and fibrin, such as streptokinase and urokinase (15). Such compounds are not suitable for the method of the invention as they result in the degradation of fibrinogen, giving rise to fibrinogen degradation products, which interfere with those resulting from fibrin degradation.

A second group of plasminogen activators is constituted by compounds described as having a high specificity for degrading fibrin compared with fibrinogen. The method of the invention advantageously exploits the specificity of this second group of compounds.

Different compounds with such fibrin specificity and/or affinity have been described in the literature. Known examples are:
- tissue plasminogen activator (t-PA) or its derivatives, such as TNK-t-PA, which is a mutant of t-PA with a very high specificity for fibrin (16);
- the activator from *Desmodus rotundus* saliva (bat-tPA or v-PA=Vampire bat salivary plasminogen activator) or its derivatives:
- DSPAs *Desmodus rotundus* salivary PAs, FEKP DSPA alpha 1 and alpha 2, EKP=DSPA beta, KP=DSPA gamma, (17);
- Staphylokinase (SAK), a polypeptide secreted by *Staphylococcus aureus* (18-19) or one of its mutants (20).

The method of the present invention is preferably carried out on a plasma sample. The soluble fibrin count is determined by measuring the degradation products resulting from the action of PA Fb sp. If necessary, the method is validated by using a positive control obtained from a normal plasma treated with traces of thrombin so as to induce coagulation activation responsible for generating soluble fibrin without, however, resulting in the formation of a clot.

To obtain the positive plasma control, the plasma is initially incubated with thrombin or other coagulation activator for a set period. The coagulation process that is then initiated is subsequently blocked by adding an activator inhibitor to prevent the reaction from continuing. When this activator is thrombin, hirudin or heparin are used as the inhibitor, for example.

The plasma incubation period and the concentrations of the coagulation activator and blocking inhibitor are advantageously determined so as to obtain all of the coagulation activation steps that precede the onset of clot formation.

Incubation in the presence of a coagulation activator (thrombin) is preferably carried out for an incubation period of 2 minutes, at ambient temperature. The inhibitor is then added in a large excess to ensure that coagulation is blocked.

If hirudin is used, it is advantageously employed in a final concentration of 100 µg/ml for a final thrombin concentration of 0.18 U/ml.

If heparin is used, it is used in a final concentration of 500 U/ml when the final concentration of thrombin used is 0.18 U/ml.

Evaluation of the soluble fibrin of the present invention employs a first step for degrading the soluble fibrin with PA Fb sp, followed by measuring the specific degradation products resulting from the action of PA Fb sp.

It is vital that the results of the method of the invention are obtained as rapidly as possible, while being representative of the quantity of soluble fibrin present in the sample. To this end, the conditions for use of PA Fb sp must be determined such that degradation of the soluble fibrin is rapid and such that it is not accompanied by "contaminating" degradation of the circulating plasmatic fibrinogen, giving rise to degradation products interfering with those originating from soluble fibrin in the assay.

The doses of PA Fb sp are selected so as to induce the greatest increase in the count of fibrin degradation products in the positive controls, and a practically zero increase in the negative controls (i.e., not treated with a coagulation activator).

Different fibrinolysis activators allowing specific degradation of fibrin can be used in the context of the present invention. Advantageously, the PA Fb sp is selected from the group formed by the activators cited above, namely: t-PA or its derivative, v-PA or its derivatives, and SAK or one of its mutants. Preferably, t-PA or SAK is used, more preferably tPA.

When the samples are incubated for 15 minutes at 37° C., the final concentration of staphylokinase used is in the range 1 to 12 µg/ml. The final retained concentration is 10 µg/ml. The incubation period can be modified and its variation is determined as a function of the nature and concentration of the PA Fb sp used.

The t-PA is advantageously used in final concentrations in the range of 1 to 2.5 µg/ml. Preferably, the t-PA is used in a concentration of 2 µg/ml.

Different soluble fibrin degradation products exist that can be specifically detected. In a preferred implementation, the D-dimer count resulting from the action of PA Fb sp on soluble fibrin is measured, i.e., the concentration of D-dimers resulting from the action of PA Fb sp on soluble fibrin is evaluated (D-dimers after the action of PA Fb sp-base D-dimers before the action of PA Fb sp).

The D-dimers resulting from the degradation of soluble fibrin in the presence of PA Fb sp can be assayed using any routine assay technique such as enzyme linked immunosorbent assay (ELISA) type methods, latex bead agglutination sensitive methods, immunochromatography methods, etc. Examples of different commercially available D-dimer assay tests that can be cited are ASSERACHROM D-Di or STA LIATIEST D-Di, both sold by Diagnostica Stago. However, within the context of the present invention, the conditions for use of the ELISA test from ASSERACHROM D-Di have advantageously been modified to shorten the test (15 mm incubation with immobilised antibody and 15 minutes with the peroxidase-labelled antibody).

In addition to the DD/E fragment, other fibrin degradation products exist, such as YD/DY, YD/DXD complexes, which can be evaluated.

As illustrated in the following examples (see Example no. 3), the method of the invention can be carried out on patients presenting with a coagulation activation either before commencing therapy or during anti-coagulating treatment or after stopping anti-coagulant therapy. It allows not only the change in a coagulation activation process to be evaluated, in particular in the context of coagulation activation diagnosis, but also allows the effectiveness of an anti-coagulant therapy to be evaluated.

In a further aspect, the present invention concerns a kit for assaying the dose of soluble fibrin in a sample, characterized in that it comprises:

a positive control for the presence of soluble fibrin obtained using the protocol described above;
a negative control constituted by a control plasma;
PA Fb sp in individual quantities for a sample or in a quantity sufficient for multiple samples;
a reagent for assaying D-dimers; and
optionally, a buffer for diluting samples, such as a pH 7.4 phosphate buffer containing 0.1% of foetal calf serum and 0.05% of Tween 20.

The positive and negative plasma controls are advantageously freeze-dried.

The preferred PA Fb sp is t-PA.

The D-dimers are assayed, for example, with a reagent for an ELISA type method, such as ASSERACHROM D-Di, or a reagent for a test sensitive to latex particle agglutination, such as STA LIATEST D-Di, both sold by Diagnostica Stago.

The following examples illustrate the present invention.

EXAMPLE N° 1

Choice of Thrombin Concentration Used to Obtain a Positive Plasma Control Comprising Soluble Fibrin The positive plasma control was prepared using the following protocol:

| Normal plasma | 300 µl |
| Human thrombin (Stago ref. 00896), 2 U/ml | 30 µl |
| Incubation, 2 min at laboratory temperature | |
| Hirudin (Knoll) | 100 µg/ml (final concentration) |
| or Heparin (Choay) | 500 u/ml (final concentration) |

Verify:
that there is no clot formation in the tube.
that a commercially available soluble fibrin detection test is positive (eg., FS test from Stago).
Two possibilities shown in Table I can be retained.

TABLE I

| I-A: Tube 2 retained. | | | | |
|---|---|---|---|---|
| Tube no | 1 | 2 | 3 | 4 |
| Citrated normal plasma | 300 µl | 300 µl | 300 µl | 300 µl |
| Thrombin | 30 µl at 4 U/ml | 30 µl at 2 U/ml | 30 µl at 1 U/ml | 30 µl at 0.5 U/ml |
| | Incubation for 2 minutes at ambient temperature | | | |
| Presence of clot | + | − | − | − |
| Heparin or | 500 units | 500 units | 500 units | 500 units |
| hirudin | 100 µg | 100 µg | 100 µg | 100 µg |
| I-B: Tube 3 retained | | | | |
| Tube no | 1 | 2 | 3 | 4 |
| Citrated normal plasma | 300 µl | 300 µl | 300 µl | 300 µl |
| Thrombin | 30 µl at 4 U/ml | 30 µl at 2 U/ml | 30 µl at 1 U/ml | 30 µl at 0.5 U/ml |
| | Incubation for 10–15 minutes at ambient temperature | | | |
| Presence of clot | + | + | − | − |
| Heparin or | 500 units | 500 units | 500 units | 500 units |
| hirudin | 100 µg | 100 µg | 100 µg | 100 µg |

EXAMPLE N° 2

Determination of Quantity of PA Fb sp to be Used Under Defined Incubation Conditions To carry out the method of the invention, the quantity of activator to be added to the sample must be such that it induces significant generation of D-dimers in the positive control plasma, as obtained in Example n° 1, and an insignificant generation of D-dimers in a negative plasma control (control not treated with thrombin).

Incubation of control plasmas and positive control plasmas (n=21) was carried out with different doses of PA Fb sp for 15 minutes at 37° C. At the end of the incubation period, the D-dimers were determined by Liatest or by rapid ELISA (D-Di Stago) (incubation for 15 minutes at 37° C. with capture antibodies and 15 minutes at 37° C. with revealing antibodies).

The results shown in Table I were obtained with the ELISA test.

Substantially analogous results were obtained with the Liatest (n=5).

TABLE II

Degradation of soluble fibrin by increasing quantities of t-PA and SAK

|  | D-dimers (ng/ml) | | Soluble fibrin (ng/ml) | |
|---|---|---|---|---|
|  | Negative control | Positive control (treated with thrombin) | Negative control | Positive control (treated with thrombin) |
| Without PA Fb sp addition | 375 | 375 |  |  |
| Staphylokinase |  |  |  |  |
| 10 µg/ml | 400 | 1750 | <50 | 1375 |
| 2 µg/ml | 390 | 1615 | <50 | 1225 |
| 1.5 µg/ml | 375 | 1700 | <50 | 1325 |
| 1 µg/ml | 350 | 1657 | <50 | 1305 |
| 0.5 µg/ml | 410 | 1125 | <50 | 715 |
| t-PA |  |  |  |  |
| 2 µg/ml | 350 | 1790 | <50 | 1415 |
| 1 µg/ml | 360 | 1420 | <50 | 1045 |
| 0.5 µg/ml | 360 | 1210 | <50 | 835 |

The dose of PA Fb sp selected is that which induces:

an increase of <300 ng/ml in untreated control plasmas (negative controls);

the greatest increase in positive control plasmas.

From these results, it appears that the preferred final concentrations of PA Fb sp to be used are:

2 µg/ml for t-PA: under these conditions, the dose of t-PA that can be neutralised by PAI is negligible;

10 µg/ml for SAK (lower doses of SAK have caused poor degradability of soluble fibrin in some patients or some positive controls, probably due to the presence of anti-staphylokinase in the sample, which anti-staphylokinase can appear as a result of staphylococcus infection).

EXAMPLE N° 3

Results Obtained with Healthy Volunteers and in Patients Presenting with Suspected Activation of Coagulation (Due to an Increase in D-Dimers)

The method was carried out on two plasma samples using the protocol indicated above:

incubating the plasmas for 15 minutes at 37° C. in the presence of t-PA (2 µg/ml) or SAK (10 µg/ml).

The D-dimers generated were assayed using an ELISA test as described above.

A. Results Obtained with Healthy Volunteer

TABLE III

|  | S.F. (ng/ml) |
|---|---|
| Control plasmas + t-PA (n = 21) | 147 ± 100 ng/ml |
| Control plasmas + IIa + t-PA (n = 21) | 2128 ± 1219 ng/ml (extreme values: 742–3660) |
| Control plasmas + SAK (n = 11) | 64 ± 82 ng/ml (extreme values: 0–215) |
| Control plasmas + IIa + SAK (n = 11) | 1700 ± 1880 ng/ml (extreme values: 250–5000) |

B. Results Obtained with Patients Presenting with Elevated D-Dimer Count (Experiment Carried Out by Rapid ELISA)

TABLE IV

Examples found in our study:

| | D-dimer count after adding t-PA (ng/ml) | D-dimer count before adding t-PA (ng/ml) | Soluble fibrin count (ng/ml) |
|---|---|---|---|
| Patient from group 1 | 5420 | 510 | 4910 |
| Patient from group 2 | 1316 | 1234 | 82 |
| Patient from group 3 | 30162 | 20699 | 9463 |

CONCLUSIONS

The method of the invention can separate the patients into three groups, depending on their soluble fibrin and D-dimer plasma counts. The characteristics of each of these three groups are summarised in Table V below:

| | Soluble fibrin (ng/ml) | D-dimers (ng/ml) | Conclusion |
|---|---|---|---|
| Group 1 | >500 | +/− | Formation of a clot that is not yet degraded |
| Group 2 | <300 | +/+++ | Presence of a thrombus, but coagulation halted |
| Group 3 | >500 | +++ | Coagulation persists, associated with degradation of clot. |

As indicated above, the method of the invention not only allows the change in the coagulation activation process to be followed, but it can also evaluate the efficiency of an anti-coagulant drug, and can ascertain whether stopping the drug re-activates coagulation.

Group 1: early coagulation activation with an increase in soluble fibrin, without elevating the D-dimers.

Group 2: patients for whom coagulation activation is halted (effective drug) but the thrombus already formed continues to degrade (normal soluble fibrin count, D-dimer count elevated).

Group 3: patients presenting with coagulation activation with clot degradation in vivo (simultaneous elevation of soluble fibrin and D-dimers): drug not effective enough.

EXAMPLE N° 4

Summary of technique employed:
Reagents:
pH 7.4 buffer
Purified human thrombin (Stago, ref 00896)
t-PA (Boehringer)
Aprotinin. Store solution at 4° C.
D-Dimer kit.
The method employed is summarised in Table VI.

TABLE VI

Protocol employed to assay soluble fibrin by D-dimer generation.

| | |
|---|---|
| Plasma | 200 |
| t-PA (20 µg/ml) (final conc. 2 µg/ml) | 20 |
| Keep at 37° C. for 15 min | |

TABLE VI-continued

Protocol employed to assay soluble fibrin by D-dimer generation.

| | |
|---|---|
| Aprotinin | 20 |
| Dilute sample as function of base D-dimers (1/20–1/1000) | |
| Plate Asserachrom D-Di | |
| Diluted sample | 200 |
| Cover wells and keep at 37° C. for 15 min | |
| Wash three times | |
| Human anti-D fragment labelled with peroxidase | 200 |
| Cover wells and keep at 37° C. for 15 min | |
| Wash three times | |
| OPD/$H_2O_2$ substrate | 200 |
| Wait precisely three minutes for each sample, then add: | |
| either 3 M $H_2SO_4$ | 50 |
| or 1 M HCl | 100 |
| Measure absorbance at 492 nm | |

REFERENCES

1. GODAL H. C., ABILGAARD U.: "Gelation of soluble fibrin in plasma by ethanol". Scand. J. Haematol., 3, 342-350, 1966.
2. BREEN F. A., TULLIS J. L.: "Ethanol gelatlon: a rapid screening test for intravascular coagulation" Ann. Intern. Med., 69, 1197-1206, 1968.
3. LIPINSKI B., WOROWSKI K.: "Detection of soluble fibrin monomer complexes in blood by means of protamine sulphate test". Thromb. Diath. Haemorrh., 20, 44-49, 1968.
4. SEAMAN A. J.: "The recognition of intravascular dotting. The plasma protamine paracoagulation test". Arch. Intern. Med., 125, 1016-1021, 1970.
5. LATALLO Z. S., WEGRZYNOWICZ S., BUDZUNKI A. Z.: "Effect of protamine sulphate on the solubility of fibrinogen, its derivatives and other plasma proteins". Scand. J. Haematol., suppl., 13, 151-162, 1971.
6. MUSUMECI V.: "Ethanol gelation test and protamine sulphate test in diagnosis of intravascular coagulation". Scand. J. Haematol., suppl. 13, 197-202, 1971.
7. NIEWIAROWSKI S., GUREWICH V.: "Laboratory identification of coagulation. The serial dilution protamine sulfate test for the detection of fibrin monomer and fibrin degradation products". J. Lab. Clin. Med., 77, 665-676, 1971.
8. KIDDER W. R., LOGAN L. J., RAPAPORT S. I., PATCH M. J.: "The plasma protamine paracoagulation test—Clinical and laboratory evaluation". A.J.C.P., 58, 675-686, 1972.
9. GUREWICH V., LIPINSKI B., LIPINSKA I.: "A comparative study of precipitation and paracoagulation by protamine sulphate and ethanol gelation tests". Thromb. Res., 2, 539-556, 1973.

10. GERRITS W. B. J., PRAKKE E. M., VAN DER MEER J., VREEKEN J.: "Causes of a negative ethanol gelation test in diffuse intravascular coagulation". Thromb. Diath. Haemorrh., 31, 299-308, 1974.
11. LARGO R., HELLER V., STRAUB P. W.: "Detection of soluble intermediates of the fibrinogen-fibrin conversion using erythrocytes coated with fibrin monomers". Blood, 47,991-1002, 1976.
12. SORIA J., SORIA C., DE RODRIGUEZ S., HORELLOU M. H., SAMAMA M., BILSKI-PASQUTIER G.: "Recherche des complexes solubles de fibrine par un test d'hëmagglutination—Applications cliniques". Presse Mëd., 6, 43, 4045-4048, 1977.
13. DEMPFLE C E., DOLLMAN M., LILL H., PUZZOVIO D., DESSAUER A., HEENE D L.: "Binding of a new monoclonal antibody against N-terminal heptapeptide of fibrin alpha-chain to fibrin polymerization site "A": effects of fibrinogen and fibrinogen derivatives, and pretreatment of samples with NaSCN. Blood Coagul. Fibrinolysis, 4, 79-86, 1993.
14. SOE G., KOHNO I., INUZUKA K., ITOH Y., MATSUDA M.: "A monoclonal antibody that recognizes a neoantigen exposed in the E domain of fibrin monomer complexed with fibrinogen or its derivatives: its application to the measurement of soluble fibrin in plasma. Blood, 88, 2109-2117, 1996.
15. GUREWICH V., HYDE E., LIPINSKI B.: "The resistance of fibrinogen and soluble fibrin monomer in blood to degradation by a potent plasminogen activator derived from cadaver limbs". Blood, 46, 555-565, 1975.
16. CANNON C P, GIBSON C M, MCCABE C H, ADGEY A A, SCHWEIGER M J, SEQUEIRA R F, GROLLIER G, GJUGLIANO R P, FREY M, MUELLER H S, STEINGART R M, WEAVER W D, VAN DE WERF F, BRAUNWALD E.: "TNK-tissue plasminogen activator compared with front-loaded altephase in acute myocardial infarction results of the TIMI 10B trial". Thrombolysis in Myocardial Infarction (TIMI) 10 B Investigators, Circulation 98 (25), 2805-14, 1998.
17. BRINGMANN P, GRUBER D, LIESE A, TOSCHI, L, KRATZCHMAR J, SCHLEUNING W D, DONNER P.: "Structural features mediating fibrin selectivity of vampire bat plasminogen activators". J Biol Chem, 270, 25596-603, 1995.
18. COLLEN D.: "Staphylokinase: a potent, uniquely fibrin-selective thrombolytic agent". Nat Med, 4-279-84, 1998.
19. SAKHAROV D V, BARRERTT-BERGSHOEFF M, HEKKENBERG R T, RIJKEN D C.: "Fibrin-specificity of a plasminogen activator affects the efficiency of fibrinolysis and responsiveness to ultrasound: comparison of nine plasminogen activators in vitro". Thromb Haemos, 81, 605-12, 1999.
20. COLLEN D, BERNAERTS R, DECLERCK, P, DE COCK F, DEMARSIN E, JENNE S. LAROCHE Y, LIJNEN H R, SILENCE K, VERSTREKEN M.: "Recombinant staphylokinase variants with altered immunoreactivity. I: Construction and characterization". Circulation, 94, 197-206, 1996.

The invention claimed is:

1. A method for assaying soluble fibrin in a sample, comprising:
measuring a difference in a count of D-dimer fibrin degradation products between a sample including Plasminogen Activator with a high specificity and/or high affinity for soluble Fibrin (PA-Fb sp) and said sample excluding said PA-Fb sp, wherein said sample which includes PA-Fb sp is incubated for minutes at 37° C. in the presence of a PA-Fb sp and said difference is then measured, wherein said PA-Fb sp is tissue plasminogen activator (t-PA) in a final concentration of about 1 µg/ml to about 2.5 µg/ml of the sample or is staphylokinase (SAK) in a final concentration of about 1 µg/ml to about 12 µg/ml of the sample.

2. The method according to claim 1, wherein the sample is plasma.

3. The method according to claim 1, wherein the assay techniques used to measure soluble fibrin degradation products are enzyme linked immunosorbent assay (ELISA) or LIATEST® methods.

4. The method according to claim 1, wherein said PA-Fb sp is t-PA in a final concentration of about 2 µg/ml of said sample.

5. The method according to claim 1, wherein said amount of soluble fibrin degradation product resulting from PA-Fb sp activation is determined with respect to a positive control, wherein said positive control is prepared from normal plasma treated with a coagulation activator then with an inhibitor of said activator to avoid formation of a clot.

6. The method according to claim 5, wherein said sample is blood and wherein said positive control is prepared from normal plasma treated with thrombin so as to induce in vitro coagulation activation, then with hirudin or heparin to avoid the formation of a clot.

7. The method according to claim 6, wherein said positive control is brought into contact with a PA-Fb sp under conditions analogous to those that are applied to the test sample.

8. A method for assaying soluble fibrin in a sample, comprising: generating D-dimer degradation products by contacting said sample with a Plasminogen Activator with a high specificity and/or high affinity for soluble Fibrin (PA-Fb sp) and comparing the count of D-dimer degradation products to said sample where D-dimer degradation products were not generated using PA-Fb sp, wherein said sample which induces PA-Fb sp is incubated for 15 minutes at 37° C. in the presence of a PA-Fb sp and said difference is then measured, wherein said PA-Fb sp is t-PA in a final concentration of about 1 µg/ml to about 2.5 µg/ml of the sample or is SAK in a final concentration of about 1 µg/ml to about 12 µg/ml of the sample.

9. A method for evaluating a change in a coagulation activation process in a sample, comprising:
measuring a difference in a count of fibrin degradation products between a sample including Plasminogen Activator with a high specificity and/or high affinity for soluble fibrin (PA-Fb sp) and said sample excluding said PA-Fb sp; and evaluating said change in a coagulation activation process, wherein said sample which includes PA-Fb sp is incubated for 15 minutes at 37° C. in the presence of a PA-Fb sp and said difference is then measured, wherein said PA-Fb sp is t-PA in a final concentration of about 1 µg/ml to about 2.5 µg/ml of the sample or is SAK in a final concentration of about 1 µg/ml to about 12 µg/ml of the sample.

10. A method for evaluating the efficacy of an anti-coagulant drug in a sample, comprising:
measuring a difference in a count of fibrin degradation products between a sample including Plasminogen Activator with a high specificity and/or high affinity for soluble fibrin (PA-Fb sp) and said sample excluding said PA-Fb sp; and monitoring said change in said coagulation process to evaluate the efficacy of said anti-coagulant drug, wherein said sample which includes PA-Fb sp is incubated for 15 minutes at 37° C. in the presence of a PA-Fb sp and said difference is then measured, wherein said PA-Fb sp is t-PA in a final concentration of about 1 µg/ml to about 2.5 µg/ml of the sample or is SAK in a final concentration of about 1 µg/ml to about 12 µg/ml of the sample.

11. A method for assaying soluble fibrin in a sample, comprising:
measuring a difference in a count of fibrin degradation products between a sample including Plasminogen Activator with a high specificity and/or high affinity for soluble fibrin (PA-Fb sp) and said sample excluding said PA-Fb sp, wherein said sample which includes PA-Fb sp is incubated for 15 minutes at 37° C. in the presence of said PA-Fb sp and said difference is then measured, and wherein said PA-Fb sp is t-PA in a final concentration of about 1 µg/ml to about 2.5 µg/ml of the sample.

* * * * *

UNITED STATES PATENT AND TRADEMARK OFFICE
CERTIFICATE OF CORRECTION

PATENT NO. : 8,883,433 B2
APPLICATION NO. : 10/373614
DATED : November 11, 2014
INVENTOR(S) : Bibi Shah Soltan Mirshahi et al.

It is certified that error appears in the above-identified patent and that said Letters Patent is hereby corrected as shown below:

In the Specification

Column 1, line 41-"less explosive and thus," should read --less explosive and, thus,--.

Column 1, line 63-"stopped and in contrast," should read --stopped and, in contrast,--.

Column 3, line 11-"into contact with a Pa-Fb" should read --into contact with Pa-Fb--.

Column 3, line 26-"degradation products is used" should read --degradation products are used--.

Column 5, line 13-"such as enzyme linked" should read --such as enzyme-linked--.

In the Claims

Column 11, line 67-"Fb sp is incubated for minutes" should read --Fb sp is incubated for 15 minutes--.

Column 12, line 11-"are enzyme linked" should read --are enzyme-linked--.

Column 12, line 37-"induces PA-Fb sp" should read --includes PA-Fb sp--.

Signed and Sealed this
Fifteenth Day of September, 2015

Michelle K. Lee
*Director of the United States Patent and Trademark Office*